(12) United States Patent
Hajizadeh

(10) Patent No.: US 11,357,634 B1
(45) Date of Patent: *Jun. 14, 2022

(54) POSTERIOR-STABILIZED SYMMETRIC KNEE PROSTHESIS

(71) Applicant: Lento Medical Inc., Houston, TX (US)

(72) Inventor: Khatereh Hajizadeh, San Jose, CA (US)

(73) Assignee: LENTO MEDICAL, INC., Houston, TX (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/150,155

(22) Filed: Jan. 15, 2021

Related U.S. Application Data

(60) Provisional application No. 62/961,333, filed on Jan. 15, 2020.

(51) Int. Cl.
*A61F 2/38* (2006.01)
*A61F 2/30* (2006.01)

(52) U.S. Cl.
CPC ............ *A61F 2/3859* (2013.01); *A61F 2/389* (2013.01); *A61F 2002/30125* (2013.01); *A61F 2002/30242* (2013.01); *A61F 2002/3863* (2013.01)

(58) Field of Classification Search
CPC ....... A61F 2/3859; A61F 2/3868; A61F 2/389
See application file for complete search history.

(56) References Cited

U.S. PATENT DOCUMENTS

| 7,326,252 | B2 * | 2/2008 | Otto ..................... A61F 2/3886 623/20.15 |
| 7,998,203 | B2 | 8/2011 | Blum |
| 8,403,994 | B2 | 3/2013 | Maloney et al. |
| 9,023,111 | B2 | 5/2015 | Walker |
| 9,730,810 | B2 | 8/2017 | Fisher et al. |
| 9,744,044 | B2 | 8/2017 | Cohen et al. |
| 10,045,853 | B2 * | 8/2018 | Fiedler ................. A61F 2/3859 |
| 2004/0243244 | A1 * | 12/2004 | Otto ..................... A61F 2/3859 623/20.27 |
| 2009/0319049 | A1 | 12/2009 | Shah et al. |

(Continued)

FOREIGN PATENT DOCUMENTS

WO WO2001070143 A1 9/2001

*Primary Examiner* — Jason-Dennis N Stewart
(74) *Attorney, Agent, or Firm* — Mark Protsik; Thomas Schneck

(57) ABSTRACT

A knee prosthesis for total knee replacement has femoral and tibial joint components. The femoral component has a medial condyle, a lateral condyle and an intercondylar recess between the condyles. The condyles have in sagittal profile a spiral outer surface with increasing anterior-to-posterior radii of curvature, such as radii that follow a Fibonacci sequence ratio per every quadrant. The tibial component is lateral-medial mirror symmetric in coronal profile and has shallow concave medial and lateral condyle surfaces for receiving corresponding condyles of the femoral component as bearing surfaces when the femoral and tibial components are biased together under applied tension by ligaments. The shallow concave condyle surfaces in sagittal profile have sharp radii of curvature near anterior and posterior ends of the condyle surfaces that can accommodate up to 5° anterior and up to 6° posterior misplacement error and up to 4° rotational mismatch between the femoral and tibial components.

11 Claims, 7 Drawing Sheets

(56) References Cited

U.S. PATENT DOCUMENTS

| | | | |
|---|---|---|---|
| 2009/0326666 A1* | 12/2009 | Wyss | A61F 2/3886 |
| | | | 623/20.29 |
| 2009/0326667 A1* | 12/2009 | Williams | A61F 2/3868 |
| | | | 623/20.31 |
| 2013/0296860 A1 | 11/2013 | Chana et al. | |
| 2018/0021144 A1* | 1/2018 | Parisi | A61F 2/389 |
| | | | 623/20.32 |
| 2021/0113340 A1* | 4/2021 | Parisi | A61F 2/389 |

\* cited by examiner

POSTERIOR-STABILIZED SYMMETRIC KNEE PROSTHESIS

CROSS-REFERENCE TO RELATED APPLICATION

This application claims priority under 35 U.S.C. 119(e) from U.S. provisional application 62/961,333 filed on Jan. 15, 2020.

TECHNICAL FIELD

The present invention relates to a knee prosthesis for implanting in total knee replacement surgery.

BACKGROUND ART

Knee joint motion, i.e., the interaction between the distal femur and proximal tibia during flexion and extension, is quite complex. While it might seem that the tibia merely rotates relative to the femur about a coronal axis passing through the knee, there are also longitudinal rotations of the tibia relative to the femur as well as translational motions between femur and tibia. The complex knee articulation is determined by the geometry of the distal femur and proximal tibia and the arrangement of ligaments that hold the femur and tibia together.

Current prosthetic implants for total knee replacement do not address the full complexity of knee joint motion. FIG. 1 shows a typical existing knee implant of the prior art. There is a femoral component 11 and a tibial component 13, both anchored to bone of the respective femur and tibia and biased together under applied tension from attached ligaments. The femoral component 11 has medial and lateral condylar structures 15 that slide over corresponding slightly concave surfaces 17 on the tibial component. Most of the existing implants, like that seen in FIG. 1, have a simple hinge-based design providing anterior-posterior rotation only. As a result, the total amount of flexion of the knee is limited to at most about 70° to 80° on average. This will reduce a patient's quality of life after surgery.

What is needed is a knee prosthesis that more closely replicates a real knee's motion, accommodating not only a hinge-rotation motion of the knee joint, but also a translation of knee joint to allow for greater flexion. U.S. Pat. Nos. 8,403,994 and 9,023,111 and U.S. Patent Application Publication 2009/0319049 represent several different attempts to address this issue.

SUMMARY DISCLOSURE

A knee replacement prosthesis in accord with the present invention comprises a femoral component and a tibial component constructed to enable anterior-posterior translation of the femur relative to the tibia during flexion of the knee. The femoral component connects to the distal end of a resected femur and includes medial and lateral condyles having distal, articulating surfaces, and a patellar flange having a patellar articulating surface. The tibial component connects to the proximal end of a resected tibia and includes a proximal bearing surface with medial and lateral concavities shaped to articulate with the medial and lateral condyles. The femoral component has a spiral-like outer sagittal profile with increasing anterior-to-posterior radii of curvature.

The new prosthesis can also compensate for any minor position errors arising from the surgery, mainly due to internal and external rotation of the femoral and tibial components.

DETAILED DESCRIPTION

The present invention distinguishes from prior designs in that it closely mimics natural knee movement by having certain features in the tibial and femoral components. A varying curvature of the femoral component in the coronal plane accommodates rotations of up to 90°-110° (full flexion) as the knee bends and the medial collateral ligament (MCL) and anterior cruciate ligament (ACL) are loose.

It also can accommodate surgeon's error up to 3° by having specific curvatures on the tibial component. To achieve this goal, we have two features for the tibial part to accommodate femur misplacement. The profiles in the sides in addition to the curvatures on the anterior and posterior sides of tibial component provide stability to the knee implant during full extension and full flexion positions. Due to these features and the varied radius of curvature of the femoral component, the degree of implant rotation while the knee flexes is increased compared to prior designs. Therefore, in this invention, while we have a higher range of rotation, it is stable as well.

By adding these features to the prior designs, a better approximated natural kinematics compared to both modern and legacy off-the-shelf total knee implant designs is achieved, and the exhibited motion patterns more closely resemble those of a normal knee.

The choice of implant size can be based on medial-lateral (ML) and anterior-posterior (AP) dimension measurements obtained from a patients' MRI or CT scan, so that matching a prosthesis to a patient is addressed by providing a wide range of different available prosthesis sizes.

Figure 1:
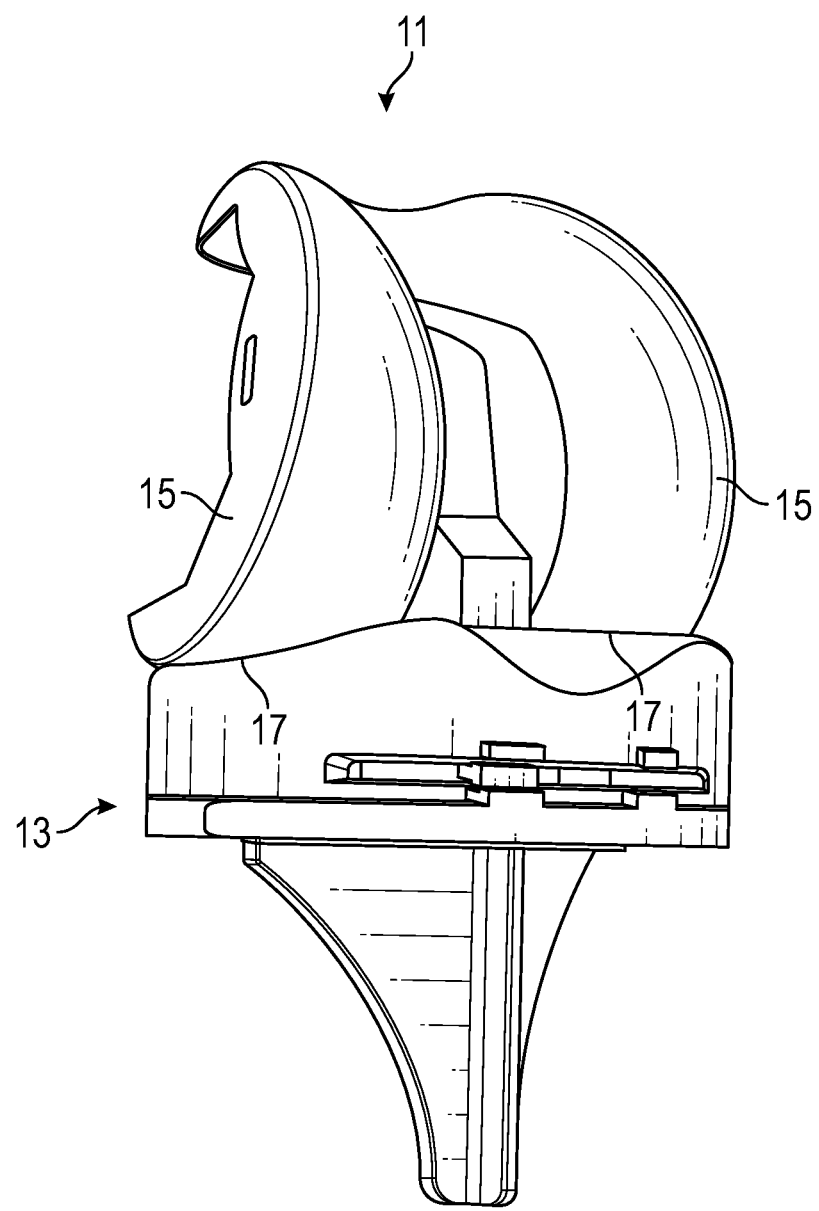
FIG. 1 shows existing knee implants of the prior art.
Figure 2:
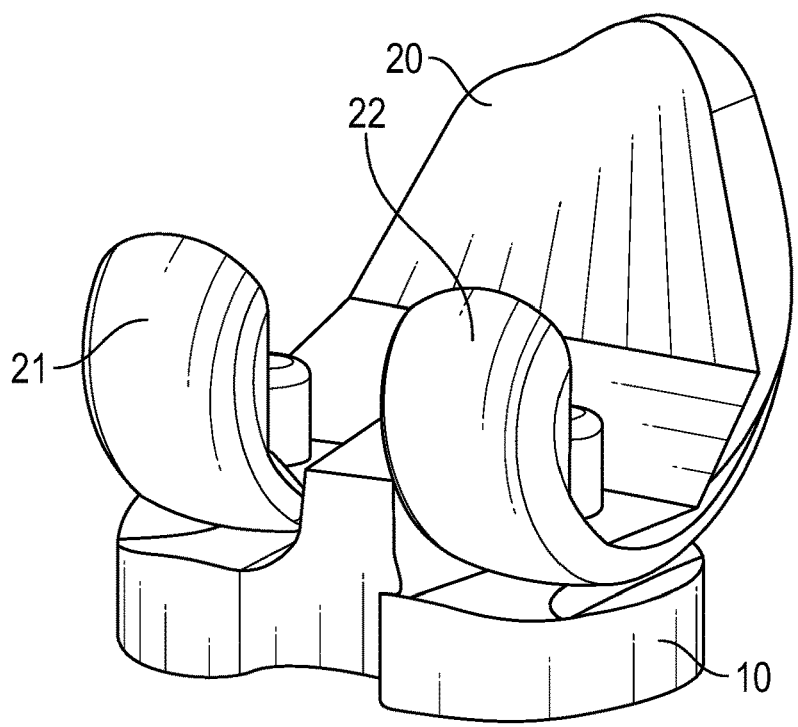
FIG. 2 is a perspective of a knee prosthesis in full extension in accordance with an embodiment of the invention showing the proximal surface of the femoral component (PS implant).
Figure 4:
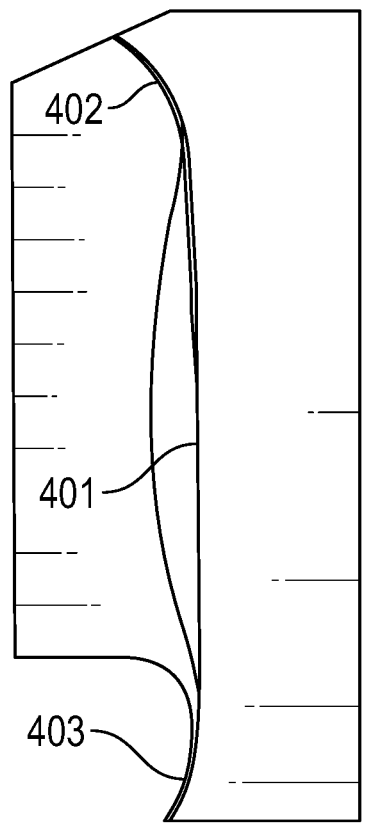
FIG. 4 is an enlarged perspective showing the side view of the tibial component.
Figure 5:
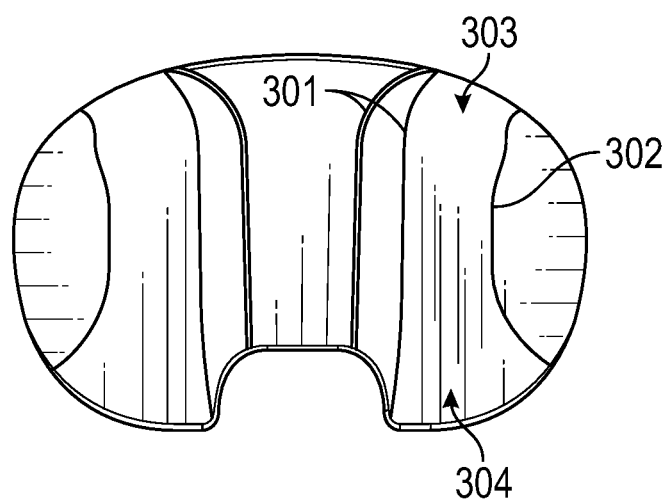
FIG. 5 is an enlarged perspective showing the top-down view of the curvatures of tibial component 10.
Figure 6:
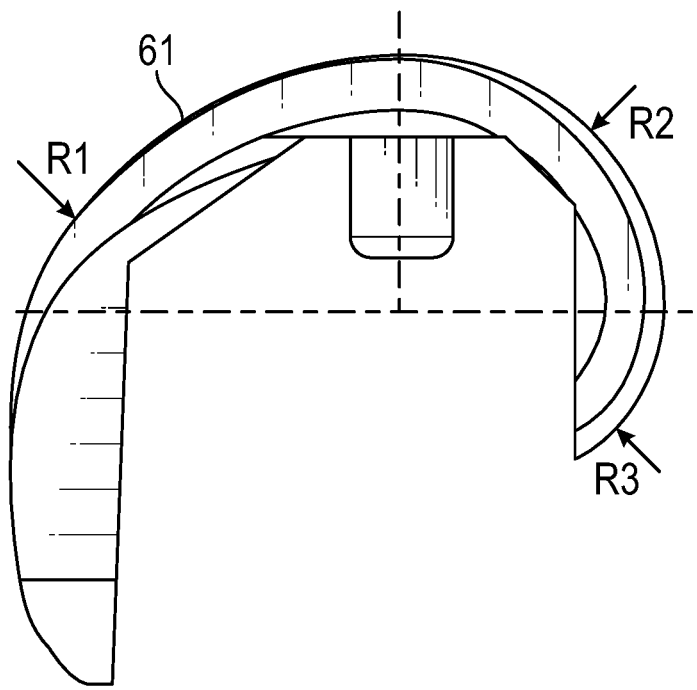
FIG. 6 is a lateral elevation of the femoral component 20.
Figure 7:
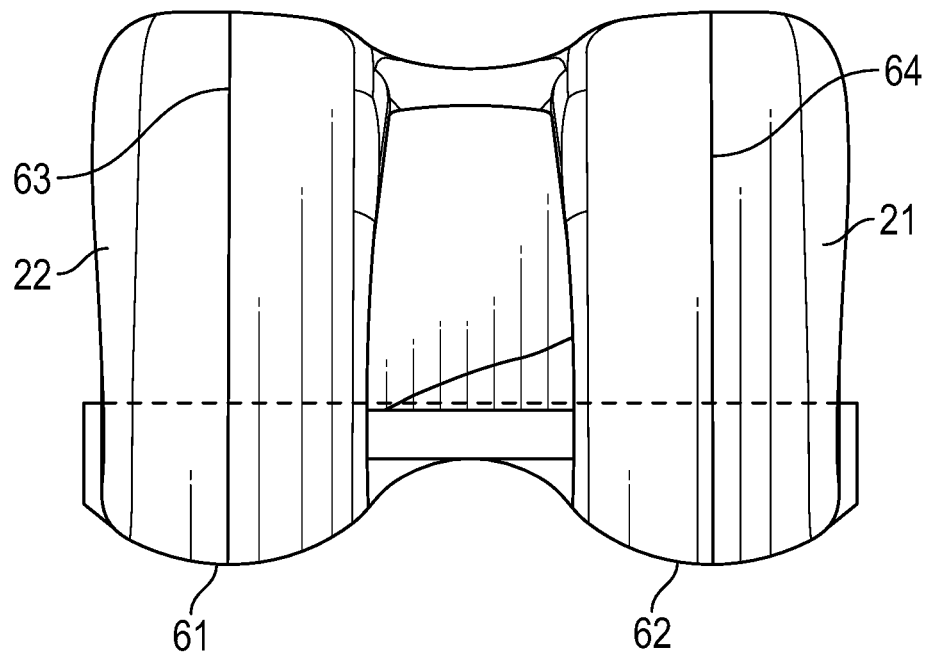
FIG. 7 illustrates the lateral and medial condyles' curvature.
Figure 8A:
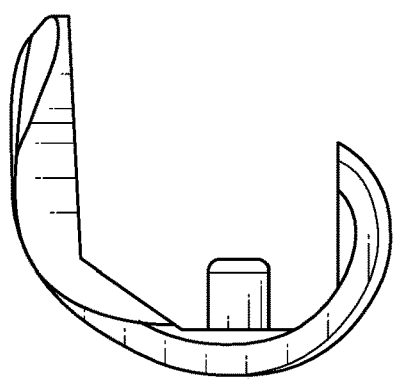
FIGS. 8A through 8E and 9A through 9E are respective sagittal and coronal views of the knee prosthesis that illustrate how the contact curvature gradually changes from a fully extended knee position to a fully flexed knee position.
Figure 9A:
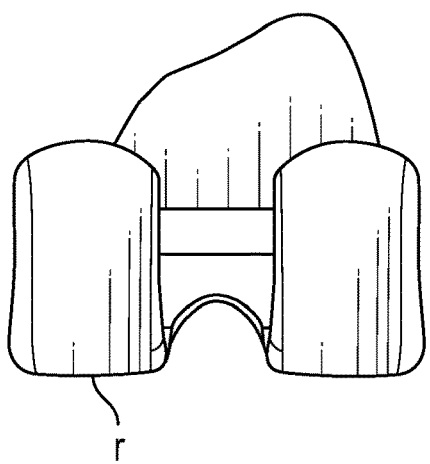
Figure 8B:
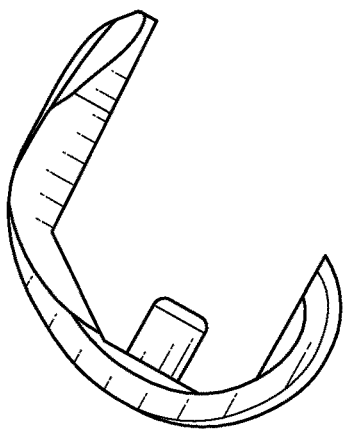
Figure 9B:
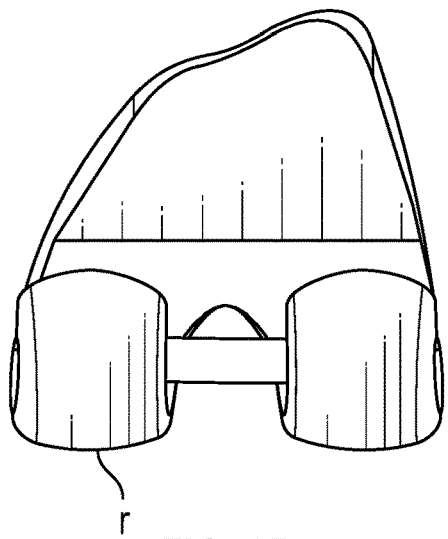
Figure 8C:
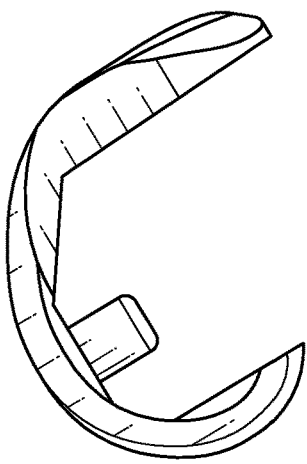
Figure 9C:
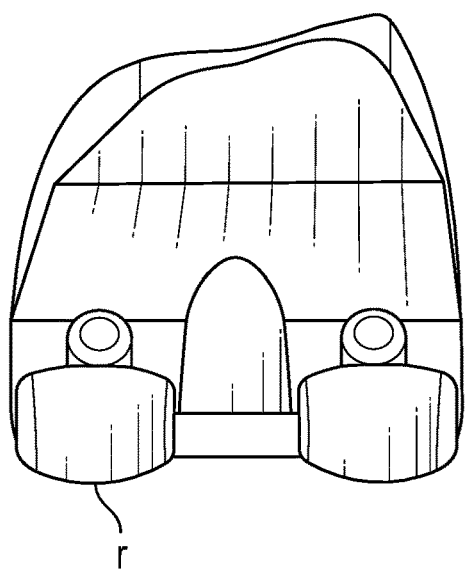
Figure 8D:
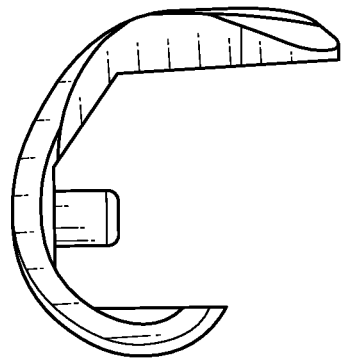
Figure 9D:
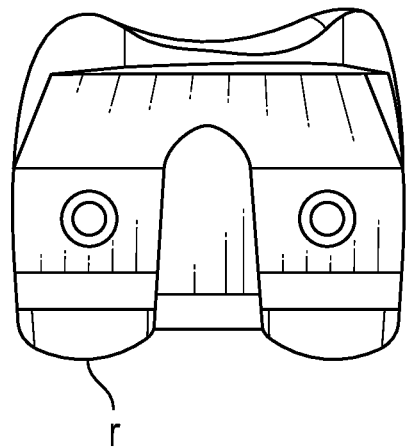
Figure 8E:
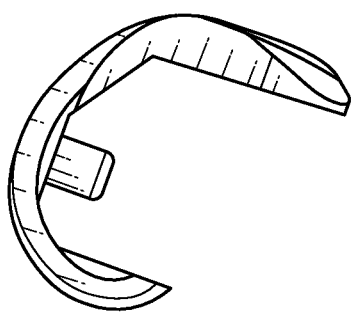
Figure 9E:
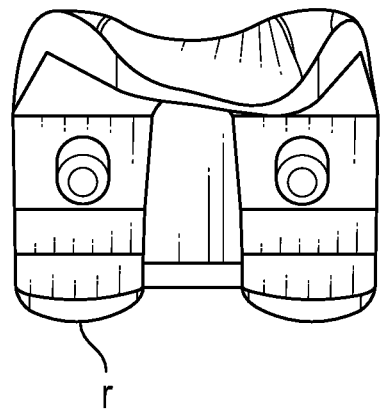

One embodiment of a knee replacement prosthesis in accord with the invention is illustrated in FIG. 2-9. FIG. 2 shows the knee implant in its full-extension position. The prosthesis includes a femoral component 20, constructed and designed to be fixed to the distal end of a resected femur, and a tibial component 10, constructed and designed to be fixed to the proximal end of a resected tibia. The tibial component 10 has a symmetrical design that can be used on either the left or right knee; that is, in coronal view there is a medial-lateral mirror symmetry of the condylar and other structures of the tibial component. The femoral component with condyles is illustrated in FIGS. 6-8 for installation on the right knee. A mirror image of the femoral component 20 will be used for installation on the left knee. The femoral component 20 has a medial condyle 21, and a lateral condyle 22. As the prosthesis flexes, different sections of the curved condylar portions engage and articulate with the tibial component 10. In the present invention, the tibial component is characterized by curves designed to accommodate the translation of the femur on the medial side beyond the 90° flex position.

It should also be noted that the implant is designed for use either with the user's original patella and patellar ligaments, or if too degraded the implant can have a patella flange either as part of or attached in front of the femoral component. Such a patella flange will be a conventional one already available in the prior art, and thus will not be discussed further.

Figure 3:
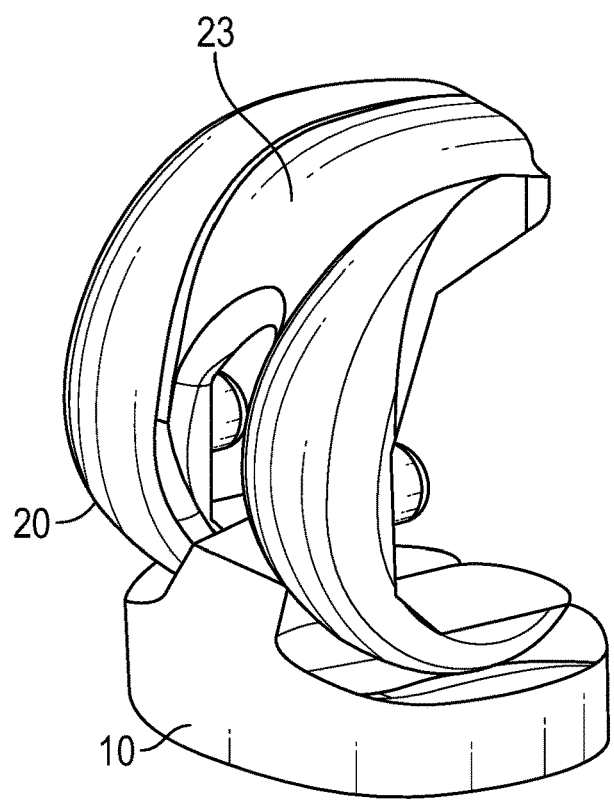
FIG. 3 is a perspective of a knee prosthesis in full flexion in accordance with an embodiment of the invention showing anterior condylar portion and implant trochlear groove of the femoral component.

The prosthesis in FIG. 3 shows the implant in a 90° flex position. An implant trochlear groove 23, which bridges the anterior ends of the medial 21 and lateral 22 condyles, respectively can be seen in this figure.

FIGS. 4-5 are schematic representations of the tibial component of the current invention.

FIG. 4 shows the side sagittal view of the tibial component in the present invention. There is a slight curvature in the middle 401 and two sharper curvatures on the anterior 402 and posterior 403 portions. Those two sharper curvatures 402 and 403 at the anterior and posterior ends act as blockers that give stability to the knee implant to mimic its natural motion.

The front coronal view of the tibial profile, which is shown in FIG. 5, exhibits three curvatures 301, 302 and 303. The middle curvature 301 can accommodate misplacement error of the femoral component. The side curvature 302 limits the rotation of femoral component according to natural safe range of knee motion. These curvatures on axial plane work all together to accommodate a 3°-5° misplacement on the anterior side 303 and a 4°-6° misplacement on the posterior side 304. This feature also accommodates enough space for femur rotation while the knee flexes.

$$1° \leq \alpha \leq 3°, \ 4° \leq \beta \leq 7°,$$

$$2° \leq \gamma \leq 4°, \ 8° \leq \varphi \leq 12°$$

Any surgeon's error of internal/external rotation (IR/ER) of one or both of the femoral and tibial components can cause a reduction of overall extension and flex of the knee joint. FIG. 5 shows that this invention accommodates α-degree mismatch of IR/ER of the components. α may vary from 1°-4°.

FIG. 6 shows the sagittal view of the femoral component. The outer surface 61 of the femoral component, which engages the tibial component, exhibits a kind of spiral profile. Specifically, in the sagittal profile, the radii of the femoral component ($R_i$) gradually increase from the posterior to the anterior side ($R_1 > R_2 > R_3$). The increase may occur for each quadrant, or alternatively at more frequent angles. The radii of the femoral component (Ri) are a function of Ø, medial-lateral (ML) and anterior-posterior (AP) dimension parameters in the sagittal plane. The Ø varies from 0.5-0.7 based on the size of the femur. Ø will be driven from the best Fibonacci number which is fitted to the anatomical knee data (AP and ML). n is the Fibonacci number which is varies from 4 to 10. $f_n$ is the $n^{th}$ number of Fibonacci series value.

$$\emptyset = f_{n+1}/f_{n-1} \text{ where } 4 < n < 10$$

$$R_i = Fr(\varphi, ML, AP)$$

FIG. 7 shows the symmetric lateral 61 and medial 62 condyle curvatures. Each condyle 21, 22 generally comprises an anterior and posterior surface, which blend smoothly with each other without any abrupt transition. These condyles will be contacted with the tibial component through the line of contacts which are shown as lateral 63 and medial 64 contact lines. In general, the major radius of curvature of the condyles 21, 22 varies from front to back to mimic anatomic femoral rollback during high degrees of flexion.

FIGS. 8A-8E and 9A-9E show another feature of this invention which is distinguished from prior designs. In this invention, without loss of any anatomical shape the curvature of the femoral part changes from posterior to anterior. The prior designs mostly have same radius circle-based feature on the femur component. The circle shape in the proximal part allows rotation when the knee is at 90-degree flex. The radius r will be changed according to the function of the anatomical knee size and the rotation of the knee. It gives the implant higher flexibility compare to prior designs.

The contact radius gradually changes when the femur rotates from full extend position (0 degree) to full extension (110 degree). This radius variation helps the femur mimic the natural knee movement. The posterior portion of femoral condyle is spherical in shape, while the anterior portion of femoral condyle is ellipsoidal in shape.

$$r = a1 + a2 \cdot f1(\text{size}, \theta)$$

$$0.01 < a1 < 0.2 \text{ and } 0.001 < a2 < 0.1$$

f1 is the function of the anatomical size and rotation of the Knee implant.

Figure 10:
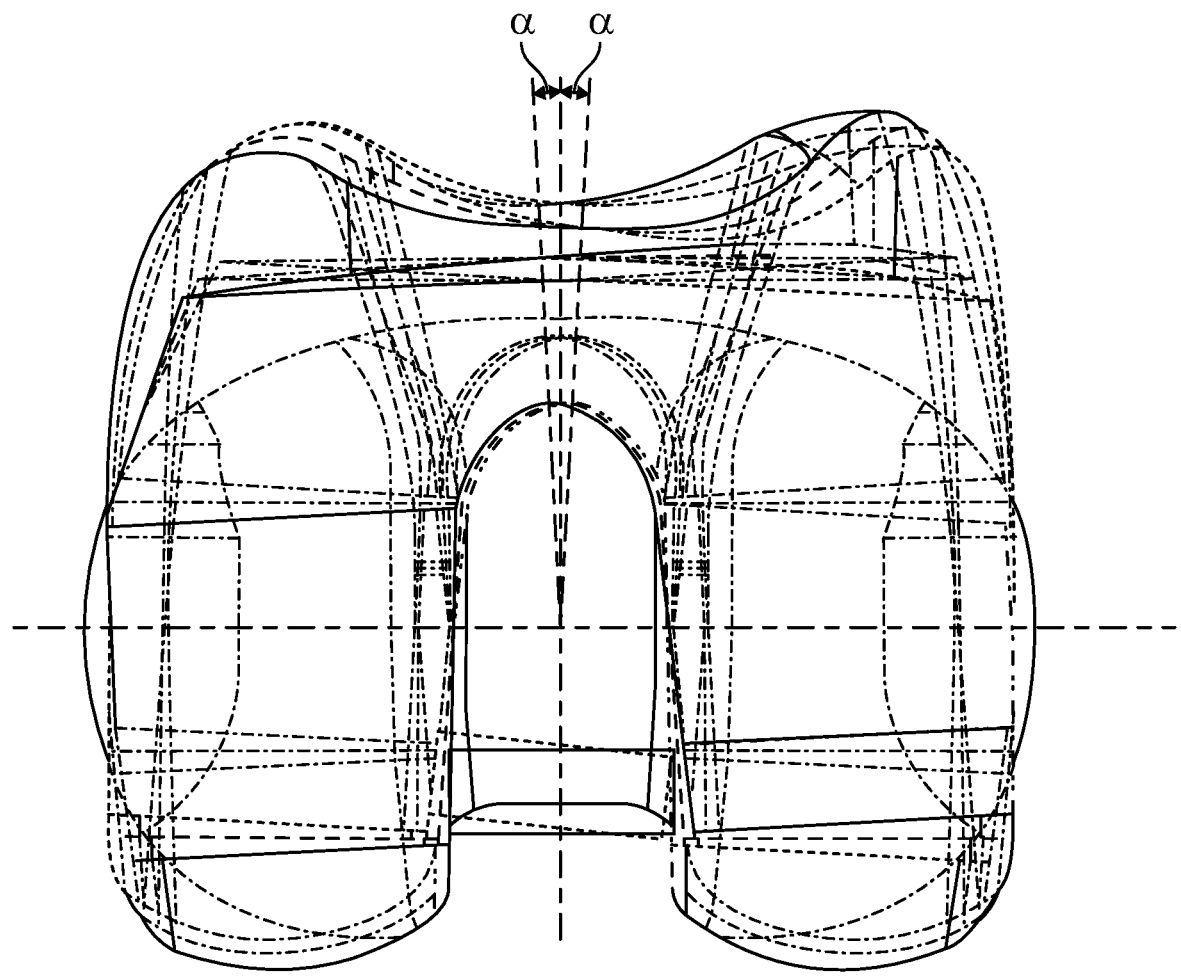
FIG. 10 is an enlarged perspective of the femoral component illustrating with a rotation.

FIG. 10 shows how the curvatures can accommodate the tibial or femoral component misplacement up to a degree.

The invention claimed is:

1. A knee prosthesis, comprising:
   a femoral joint component for attachment to a distal femur end, the femoral component having a medial condyle, a lateral condyle and an intercondylar recess between the condyles; and
   a tibial joint component for attachment to a proximal tibia end, the tibial component having shallow concave medial and lateral condyle surfaces for receiving corresponding condyles of the femoral component as bearing surfaces when the femoral and tibial components are biased together under applied tension by ligaments;
   wherein the tibial joint component being lateral-medial mirror symmetric in coronal profile, the medial and lateral condyles of the femoral joint component having in sagittal profile a spiral outer surface with increasing anterior-to-posterior radii of curvature by a Fibonacci sequence ratio per every quadrant.

2. A knee prosthesis as in claim 1, wherein the shallow concave condyle surfaces of the tibial component in sagittal profile have sharper radii of curvature near anterior and posterior ends of the condyle surfaces and a slighter curvature in middle portions of those condyle surfaces.

3. A knee prosthesis as in claim 1, wherein the shallow concave condyle surfaces of the tibial component in coronal profile have middle and side curvatures adapted to accommodate up to 5° anterior and up to 6° posterior misplacement error and up to 4° rotational mismatch between the femoral and tibial components.

4. A knee prosthesis as in claim 1, wherein posterior portions of each femoral condyle contacting the corresponding tibial condyle up to 90° flexion is substantially spherical in shape and anterior portions of each femoral condyle contacting the corresponding tibial condyle beyond 90° flexion is substantially elliptical in shape in coronal profile.

5. A knee prosthesis as in claim 4, wherein contact radii of curvature of lateral and medial condyles of the femoral component with each corresponding tibial condyle are a function of degree of flexion θ as the knee rotates from full extension to full flexion.

6. A knee prosthesis, comprising:
  a femoral joint component for attachment to a distal femur end, the femoral component having a medial condyle, a lateral condyle and an intercondylar recess between the condyles; and
  a tibial joint component for attachment to a proximal tibia end, the tibial component having shallow concave medial and lateral condyle surfaces for receiving corresponding condyles of the femoral component as bearing surfaces when the femoral and tibial components are biased together under applied tension by ligaments;
  wherein the tibial joint component being lateral-medial mirror symmetric in coronal profile, the shallow concave condyle surfaces of the tibial component in sagittal profile having sharper radii of curvature near anterior and posterior ends of the condyle surfaces and a slighter curvature in middle portions of those condyle surfaces, the condyle surfaces of the tibial component in coronal view having sharper radii of curvature at lateral and medial side extremities than those for middle curvatures near the intercondylar recess to limit rotation of the femoral component to a natural safe range.

7. A knee prosthesis as in claim 6, wherein the shallow concave condyle surfaces of the tibial component in coronal profile have middle and side curvatures adapted to accommodate up to 5° anterior and up to 6° posterior misplacement error and up to 4° rotational mismatch between the femoral and tibial components.

8. A knee prosthesis as in claim 6, wherein the medial and lateral condyles of the femoral joint component have in sagittal profile a spiral outer surface with increasing anterior-to-posterior radii of curvature.

9. A knee prosthesis as in claim 8, wherein the spiral outer surface of the femoral component in sagittal profile increases in radii of curvature by a Fibonacci sequence ratio per every quadrant.

10. A knee prosthesis as in claim 6, wherein posterior portions of each femoral condyle contacting the corresponding tibial condyle up to 90° flexion is substantially spherical in shape and anterior portions of each femoral condyle contacting the corresponding tibial condyle beyond 90° flexion is substantially elliptical in shape in coronal profile.

11. A knee prosthesis as in claim 10, wherein contact radii of curvature of lateral and medial condyles of the femoral component with each corresponding tibial condyle are a function of degree of flexion θ as the knee rotates from full extension to full flexion.

* * * * *